United States Patent
Cacciaglia et al.

(10) Patent No.: US 10,336,687 B2
(45) Date of Patent: Jul. 2, 2019

(54) SELECTED AMIDE OF γ-HYDROXYBUTYRIC ACID AND USES THEREOF IN THE TREATMENT OF ALCOHOL MISUSE

(71) Applicant: LABORATORIO FARMACEUTICO C.T. S.R.L., Sanremo (IT)

(72) Inventors: Roberto Cacciaglia, Ospedaletti (IT); Antonella Loche, Sanremo (IT)

(73) Assignee: LABORATORIO FARMACEUTICO C.T. S.R.L., Sanremo (IT)

( * ) Notice: Subject to any disclaimer, the term of this patent is extended or adjusted under 35 U.S.C. 154(b) by 0 days.

(21) Appl. No.: 15/750,047

(22) PCT Filed: Aug. 3, 2016

(86) PCT No.: PCT/EP2016/068517
§ 371 (c)(1),
(2) Date: Feb. 2, 2018

(87) PCT Pub. No.: WO2017/021438
PCT Pub. Date: Feb. 9, 2017

(65) Prior Publication Data
US 2018/0230086 A1 Aug. 16, 2018

(30) Foreign Application Priority Data
Aug. 4, 2015 (IT) .................. 102015000041820

(51) Int. Cl.
*C07C 235/06* (2006.01)
*A61K 31/165* (2006.01)
*A61P 25/30* (2006.01)
*A61P 25/32* (2006.01)
*C07C 231/02* (2006.01)

(52) U.S. Cl.
CPC .......... *C07C 235/06* (2013.01); *A61K 31/165* (2013.01); *A61P 25/30* (2018.01); *A61P 25/32* (2018.01); *C07C 231/02* (2013.01)

(58) Field of Classification Search
CPC .................................................... C07C 235/06
See application file for complete search history.

(56) References Cited

FOREIGN PATENT DOCUMENTS

WO          98/06690 A1     2/1998

OTHER PUBLICATIONS

International Search Report for PCT/EP2016/068517 dated Jan. 2, 2017.
L. Ferraro, et al., "The New Compound GET73, N-[(4-trifluoromethyl)benzyl]4-metho-xybutyramide, Regulates Hippocampsl Aminoacidergic Transmission Possibly via an Allosteric Modulation of mGlu5 Receptor. Behavioural Evidence of its "Anti-Alcohol" and Anxiolytic Properties," Current Medicinal Chemiatry, vol. 20, No. 27, pp. 3339-3357 (Jan. 1, 2013).

*Primary Examiner* — Brian E McDowell
(74) *Attorney, Agent, or Firm* — Abelman, Frayne & Schwab

(57) ABSTRACT

The present invention relates to a selected amide of γ-hydroxybutyric acid, a process of manufacture and uses thereof. The invention also includes a pharmaceutical composition comprising an effective amount of the selected compound of the invention for use in preventing or treating drug addiction, especially alcohol misuse or dependency.

3 Claims, 8 Drawing Sheets

SELECTED AMIDE OF γ-HYDROXYBUTYRIC ACID AND USES THEREOF IN THE TREATMENT OF ALCOHOL MISUSE

RELATED APPLICATIONS

This application is a national phase of International Application No, PCT/EP2016/068517 filed Aug. 3, 2016, and claims priority from Italian Patent Application No. 102015000041820 filed Aug. 4, 2015, both incorporated by reference in theft entirety.

FIELD OF THE INVENTION

The present invention relates to a selected amide of γ-hydroxybutyric acid, a process of manufacture and uses thereof.

The present invention origins in the field of anti-addiction medications in particular in the field of drugs for treating Alcohol Use Disorders (AUDs).

BACKGROUND ART

The gamma-hydroxybutyric acid or GHB is an endogenous constituent of the mammalian brain, where it exerts a role as neurotransmitter and neuromodulator.

GHB is currently used in the treatment of alcohol addiction, in particular to reduce or prevent symptoms of alcohol withdrawal and the incidence of relapse.

Typically, for pharmacological use, GHB is administered in the form of its sodium salt, known as sodium oxybate.

The pharmacokinetic profile of Sodium oxybate is characterized by some unsatisfactory aspects, including low bioavailability (about 30%) and fast elimination. In fact, although sodium oxybate is quickly absorbed after oral administration, reaching the peak plasma concentration within 30-45 minutes, it is also rapidly eliminated, with a very short half-life (about 30 minutes). This latter pharmacokinetic characteristic requires a frequency of administration corresponding to 3 times a day for obtaining a satisfactory therapeutic outcome.

The short half life of this drug represents a serious drawback since it considerably reduces patient compliance and consequently therapeutic outcomes.

Thus, there is a general need for additional drugs targeted at AUDs treatment, and respect to sodium oxybate, for a drug with a more advantageous pharmacokinetic profile.

One of the general objects of the present invention is to provide a new safe and effective drug for AUDs treatment.

A specific object of the present invention is to provide a compound for the treatment of alcoholism or of alcohol misuse having an improved activity with respect to the compound 4-methoxy-N-[[4-(trifluoromethyl)phenyl] methyl]-butanamide disclosed in WO 98/06690 A1.

SUMMARY OF THE INVENTION

The inventors have now discovered that a selected amide of γ-hydroxybutyric acid is provided with an unexpected higher efficacy with respect to known compounds, in the prevention and treatment of alcohol and/or drug dependence.

It has also been found that the selected compound of the invention has a longer duration of action than GHB and its salts.

The compound of the invention finds application in the medical field, in particular in the treatment of addiction to psychotropic substances and/or in the treatment of alcoholism and alcohol withdrawal syndrome.

According to a first aspect, the present invention provides a selected compound having the following formula (I)

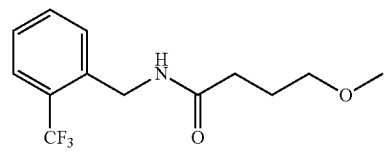

Formula (I)

According to another aspect, the present invention relates to a process for the preparation of the compound of the above formula (I), said process comprising the step of reacting a compound of formula R1 with methyl 4-methoxybutyrrate of formula R2 according to the following reaction scheme

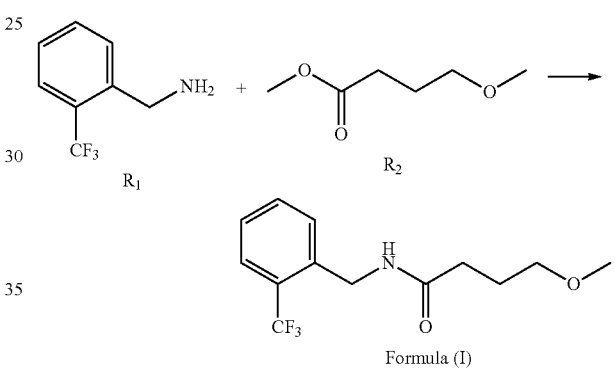

Formula (I)

According to a further aspect, the present invention relates to the use of the compound of formula (I) as illustrated above in the treatment of disorders of the CNS and/or in addiction to ethanol or treatment of alcoholism, in general.

In accordance with a yet further aspect, the present invention relates to a composition comprising a compound of formula (I) as illustrated above and at least a physiologically acceptable carrier.

The features and the advantages of the present invention will become apparent from the following detailed description and from the examples provided as an illustrative and non limiting process and from the accompanying FIGS. 1-7, in which.

DETAILED DESCRIPTION OF THE INVENTION

Figure 1:
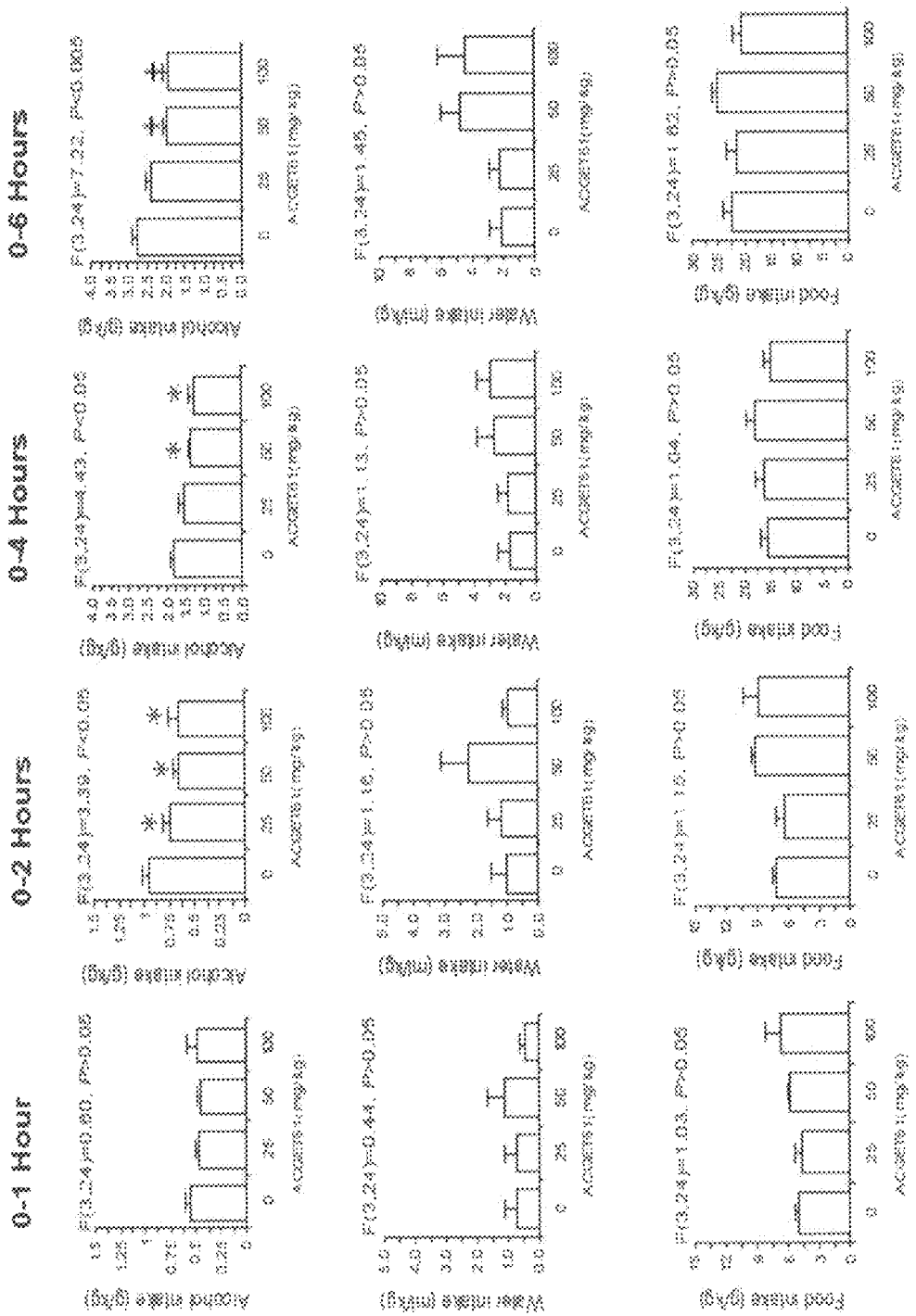
FIG. 1 shows bar graphs illustrating the effects of the compound of formula (I) identified as ACGET61 on alcohol intake in sP rats exposed to the 2 bottle free-choice regimen.
Figure 1:
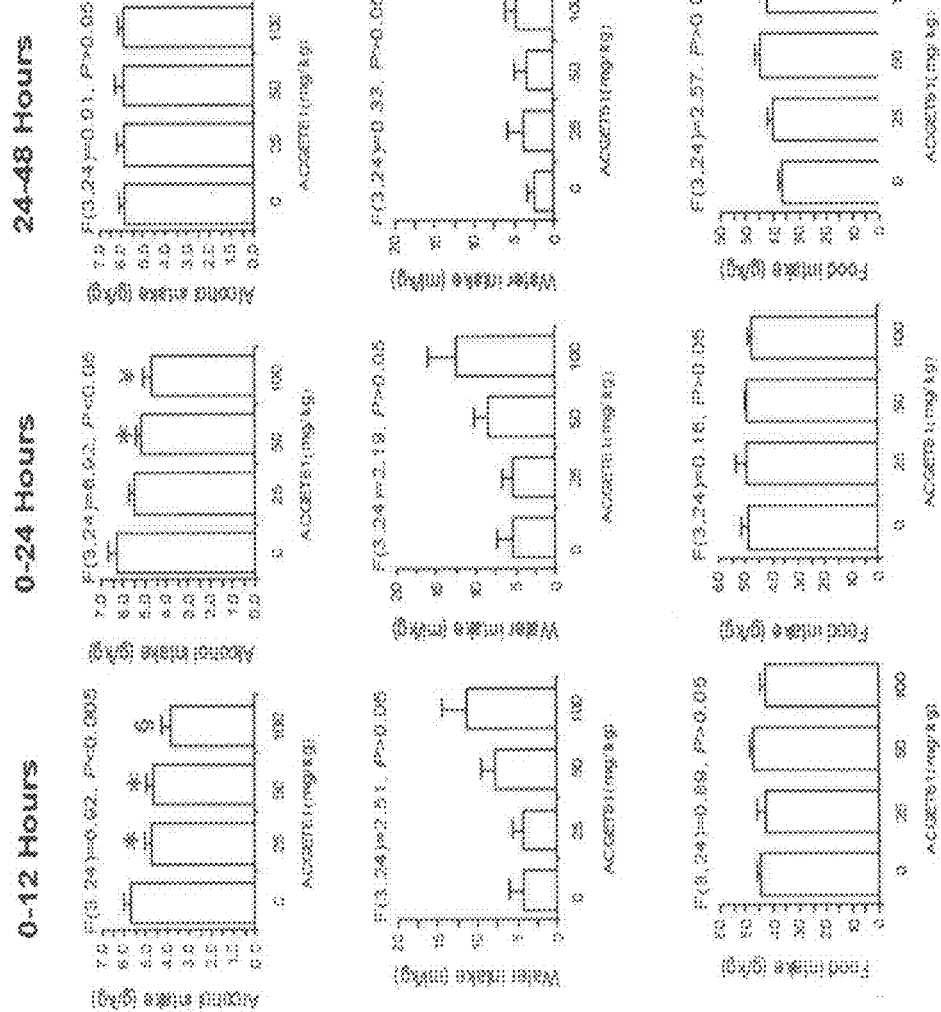

The inventors have found that a selected amide of γ-hydroxybutyric acid having formula (I) as illustrated herein below, acts as an effective negative modulator of the metabotropic glutamate receptor subtype 5 (mGluR5) and is useful specifically in the treatment of Alcohol Use Disorders.

In addition, the Applicant has found that, unexpectedly, the compound of formula (I) of the invention has an improved anti-alcohol profile with respect to its positional isomers such as GET 73.

The mechanism of action of the compound of formula (I) of the invention is based on a complex modulation targeted at metabotropic glutamate receptor of Group I, subtype 5 (mGluR5). This is a class of CNS receptors of pharmacological relevance. Experimental evidences indicate that very small structural modifications of a given compound might dramatically affect both the potency, and the type of modulation of the above receptors (Melancon et al., 2012).

Experimental evidences show that the compound of formula (I) of the invention has a high specificity for receptor of Group I, subtype 5 (mGluR5). This specificity is at the basis of its neuropharmacological properties such as the ability to reduce the alcohol consume/intake in different preclinical models and the capacity to affect the glutamate neurotransmission through a modulation of mGluR5. In addition, the compound of the invention exerts neuroprotective effects.

Thus, in accordance with a first aspect, the present invention provides a compound having the following formula (I)

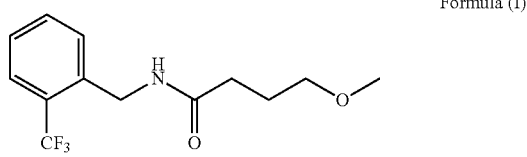

Formula (I)

The compound of Formula (I) when compared to the known amide of γ-hydroxybutyric acid GET 73 shows a longer lasting activity in reducing the alcohol consume (24 h. vs. 3 h.), an efficacy in several operant models of alcohol self-administration (see Table 1), and a greater potency in inhibiting CHPG-induced increase of glutamate in hippocampal slices (300 pM vs 500 nM). In addition, the compound of the invention has a greater potency in protecting hippocampal neurons from the damage induced by chronic exposition to alcohol (0.1 vs 1 µM) when compared to known amides of γ-hydroxybutyric acid.

These improved effects and activities of the compounds of the invention are based on the modulation of targeted metabotropic glutamate receptors of Group I, subtype 5 (mGluRs5). These receptors belong to the family C of the G-protein-coupled receptors (GPCRs). They are characterized by a seven transmembrane (7™) α-helical domain connected to a large bi-lobed extracellular amino-terminal domain. The orthosteric binding site is contained in the extracellular domain, while the currently known allosteric binding sites reside in the 7™ domain.

The mGluR family includes eight receptor type, subdivided in three groups, (Group I, II and III) based on their structure, preferred signal transduction mechanisms, and pharmacology (Schoepp et al., 1999).

Group I receptors (mGluR1 and mGluR5) are coupled to Gαq, leading to the stimulation of phospholipase C and to the increase in intracellular calcium and inositol phosphate levels. mGluR5 have been implicated in a wide range of neurological and/or psychiatric disorders, including addiction.

In the CNS, mGluR5 has been demonstrated to be expressed mainly in the cortex, hippocampus, nucleus accumbens and the caudate-putamen, brain regions known to be involved in emotional and motivational responses, memory and cognitive function.

Concerning alcohol addiction, experimental evidences indicate the importance of mGlu5 receptors in alcohol reinforcing and motivational properties and reinstatement of alcohol-seeking behavior. Furthermore, negative allosteric modulators (NAMs) of mGlu5 receptor such as MPEP, and MTEP demonstrated to be effective in reducing alcohol-seeking and relapse-like behaviors.

Based on these findings mGluR5 receptor is widely considered a valuable target for the development of new drugs aimed at treating Alcohol Use Disorders (Olive, 2009). Finally, MPEP and MTEP, have proven to be neuroprotective, providing an additional support to development of a drug potentially able to counteract the detrimental effects exerted by alcohol on the function and integrity of CNS.

The anti-alcohol profile of the compound of formula (I) is proven by the experiments reported in Example 2 which have been carried out on a well-established animal models used for the evaluation of different aspects of alcohol intake, abuse and dependency.

In another aspect thereof, the present invention relates to a process for preparing the compound of formula (I), comprising the step of:

reacting a compound of formula R1 with methyl 4-methoxybutyrrate of formula R2 according to the following reaction scheme

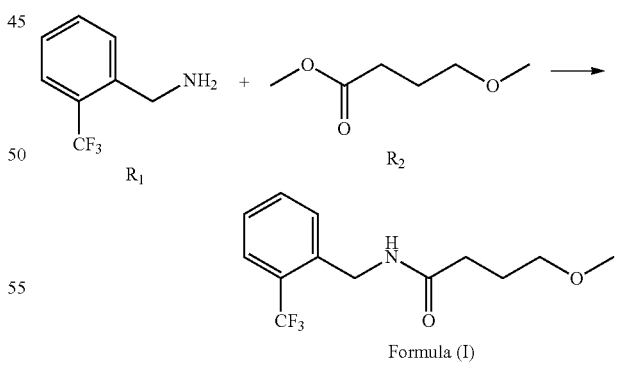

Formula (I)

In certain embodiments the above reaction is carried out in presence of a catalyser, especially $NH_4Cl$, typically in an amount of 1:5 to 1:20 with respect to the amount of R1. Preferably the catalyser, especially $NH_4Cl$ is added in an amount of 8 to 12% by weight with respect to the weight of reagent R1.

In some embodiments of the process the reagents R1 and R2 are equimolar.

In certain embodiments the reaction is carried out under heating for example in a temperature range of 120 to 170° C. preferably from 140° to 160° C.

In accordance with some embodiments the methyl 4-methoxybutyrrate R2 is prepared by reacting γ-butyrolactone R3 with Methyl orthoformate R4 typically in an acidic environment, preferably using sulphuric acid and methanol as solvent according to the following reaction scheme: 8. 7

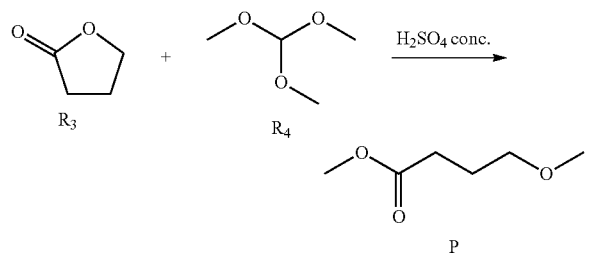

In a further aspect, the present invention relates to a pharmaceutical composition comprising the compound of formula (I) or a pharmaceutically acceptable or edible salt thereof and a pharmaceutically acceptable or edible carriers and/or excipients. As used herein, the term "salt" refers to any salt of a compound according to the present invention prepared from an inorganic or organic acid or base and internally formed salts. Typically, such salts have a physiologically acceptable anion or cation.

The compound of Formula (I) may be in crystalline form. In certain embodiments, the crystalline forms of the compounds of Formula (I) are polymorphs.

In accordance with a further aspect, the present invention relates to a composition comprising a compound of formula (I) as illustrated above and at least a physiologically acceptable carrier.

Typically the composition is a pharmaceutical composition wherein the compound of formula (I) is present in a therapeutically effective amount.

The compound of formula (I) may be administered alone or in combination with one or more active ingredients such as additional amides of γ-hydroxybutyric acid especially in the treatment of drug addiction or alcoholism or for use in reducing the chronic alcoholic desire for and habit of consuming alcoholic drinks or in the abstinence syndrome.

The pharmaceutical compositions of the present invention encompass any compositions made by mixing the compound of the present invention and a pharmaceutically acceptable carrier. Such compositions are suitable for pharmaceutical use in an animal or human.

A pharmaceutical composition may optionally contain other active ingredients. The term "carrier" refers to a vehicle, excipient, diluents, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g. oral or parenteral (including intravenous).

In preparing the compositions for oral dosage form, any of the usual pharmaceutical media may be employed, such as, for example, water, glycols, oils, alcohols, flavouring agents, preservatives, colouring agents and the like in the case of oral liquid preparations, such as, for example, suspensions, elixirs and solutions; or carriers such as starches, sugars, microcrystalline cellulose, diluents, granulating agents, lubricants, binders, disintegrating agents, and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral, including subcutaneous, intramuscular, and intravenous, nasal, rectal, topical or oral administration.

Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well known in the art of pharmacy. The preferred compositions include compositions suitable for oral administration. The oral compositions may be prepared by any of the methods well-known in the art of pharmacy.

The pharmaceutical compositions in solid form may be in the form of tablets, pills, capsules, powders, suppository and as sustained release formulations.

If desired, tablets may be coated by standard aqueous or non-aqueous techniques. In certain embodiments, such compositions and preparations may contain at least 0.5, or 1 percent of active compound. The percentage of active compound in these compositions may, of course, be varied and may conveniently be from 1 to 60%, 5 to 50%, 10 to 30 percent of the weight of the unit. The amount of active compound in such therapeutically useful compositions is such that therapeutically active dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavouring agent such as cherry or orange flavour. To prevent breakdown during transit through the upper portion of the gastrointestinal tract, the composition be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Administration of the compositions is performed under a protocol and at a dosage sufficient to reduce the dependency from drugs or alcohol intake.

In certain embodiments the pharmaceutical composition of the invention contain from 5% to 50% by weight, preferably from 10 to 30% by weight of the compound of formula (I) with respect to the total weight of the composition.

In some embodiments, in the pharmaceutical compositions of the present invention the active principle or active principles are generally formulated in dosage units. The dosage unit may contain from 1 to 2000 mg, from 10 to 1000 mg, especially from 50 to 500 mg of a compound of Formula (I) per dosage unit for daily administration.

With respect to formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Ansel's Pharmaceutical Dosage Forms and Drug Delivery Systems, 8th Edition, Lippincott Williams & Wilkins Eds., 2005, which are herein incorporated as reference.

When used in combination with one or more other active ingredients, the compound of the present invention and the other active ingredient may be used in lower doses than when each is used singly.

A preferred pharmaceutical composition is a formulation in the form for oral administration a day of the active compound according to the invention in mixture with pharmaceutical acceptable carriers, to be administered typically once a day, or in certain conditions twice or more a day.

According to another aspect thereof, the present invention provides the compound of formula (I) for use as a medicament.

In accordance with some embodiments, the present invention provides the compounds of Formula (I) for use in treating diseases or disorders associated with addiction from drugs or alcohol.

According to some embodiments, the compound of formula (I) is used in the treatment of a CNS disease and/or in the treatment of drug, alcohol addictions.

In some embodiments, the compound of formula (I) is used in the treatment of one or more diseases or disorders of the CNS selected from catalepsy, narcolepsy, insomnia, obstructive sleep apnea syndrome, depression, anxiety, insomnia associated with schizophrenia, excessive sedation, essential tremor, chronic fatigue syndrome, chronic insomnia and neuroprotection from detrimental substances.

According to a preferred embodiment the compound of formula (I) or a pharmaceutical composition containing such compound (I) as active ingredient is for use in the prevention or treatment of alcoholism, forms of dependency from alcohol, alcohol misuse, alcohol abuse, abstinence.

Typically, the compound of formula (I) or a pharmaceutical composition containing an effective amount of such compound (I) as active ingredient may be used to prevent relapse in alcohol dependent subjects, to overcome abstinence periods from alcohol intake, to limit the amount of alcohol ingested by a subject and/or to motivate a subject to change his behaviour in respect of alcohol intake.

It is to be understood that all aspects identified as preferred and advantageous for the derivative of the invention should be deemed as similarly preferred and advantageous also for the production process, the pharmaceutical compositions and the relevant uses.

In accordance to an additional aspect the invention provides a method for the prevention or treatment of drug addiction, alcohol misuse, alcohol use disorders as described hereinbefore, said method comprising the administration of an effective amount of a compound of formula (I) or a pharmaceutical composition containing such compound (I).

In an additional aspect, the present invention also concerns combination therapies or treatment with a compound of Formula (I) or pharmaceutical composition containing them. In some embodiments, the compounds of Formula (I), and their pharmaceutical compositions and methods of administering them, are useful in treating drug addiction or alcoholism when administered in combination with other pharmacological agents or active ingredients.

The following Examples are provided for illustrative and not limiting purposes.

EXAMPLES

Example 1

Preparation of the Compound of Formula (I) (Referred as ACGET61)

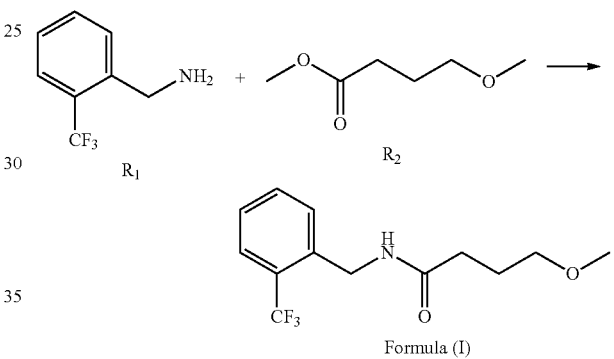

Formula (I)

In a round-bottomed flask equipped with an efficient condenser and a magnetic stirrer, $R_1$ (MW: 175.088; 4.43 g) and $R_2$ (MW: 132.16; 3.347 g) are added in an 1:1 molar ratio. $NH_4Cl$ (443 mg) is then added as catalyst (10% by weight with respect to $R_1$). The mixture is heated at 150° C. for 45 h and it assumes a deep green/dark purple color. The disappearance of the reagent is monitored by TLC (AcOEt: Hexane 1:2) using ninhydrin as detecting agent (prepared dissolving 200 mg ninhydrin in 150 ml EtOH).

When the reagent is completely disappeared, the reaction mixture is cooled and the residue is dissolved in DCM, washed three times with HCl 3N then with water till neutral pH.

The crude product thus obtained is purified by column chromatography eluting with a gradient of AcOEt:Hexane (from 1:10 to 1:1).

The pure product (ACGET61, MW 275.11) is obtained as a white/light pink solid in 64% yield.

Methyl 4-methoxybutyrate ($R_2$ Reagent) Synthesis

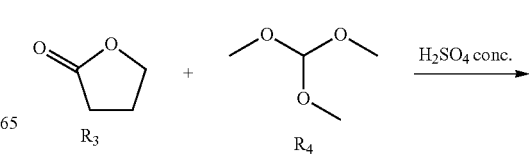

-continued

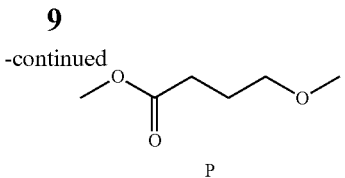

P

In a round-bottomed flask equipped with an efficient condenser and a magnetic stirrer, γ-butyrolactone $R_3$ (MW: 86.06; 1 eq; d=1.12), trimethylorthoformate $R_4$ (MW: 106.12; 1.9 eq; d=097) and concentrated sulfuric acid (1 ml per 10 ml of γ-butyrolactone $R_3$) are mixed in MeOH (4 ml per g of γ-butyrolactone $R_3$). The mixture is heated at 60° C. for 26 h under stirring. The disappearance of the reagent is monitored by TLC (AcOEt:Hexane 1:1) using Pancaldi solution as detecting agent (prepared dissolving 25 g ammonium molybdate and 5 g cerium sulphate in 450 ml $H_2O$ and 50 ml concentrated sulfuric acid).

At the end of the reaction, the solvent is evaporated under reduced pressure. The residue is dissolved in AcOEt and washed with a saturated solution of $NaHCO_3$ till pH=8.

The crude light yellow oil is distilled under vacuum (BP: 163-164° C., p: 760 Torr).

The pure product (P, MW: 132.16) is obtained as a colorless oil in 80% yield.

Example 2

Anti-Alcohol Profile of the Compound of Formula (I) (Referred as ACGET 61) in Sardinian Alcohol Preferring (sP) Rats Anti-alcohol profile of ACGET61 in Sardinian alcohol preferring (sP) rats Sardinian alcohol preferring (sP) rats represents one of the few rat lines selectively bred worldwide for high ethanol preference and consumption (Colombo et al., 2006) and are utilized in multiple experimental procedures validated for the evaluation of different aspects of alcohol drinking. These experimental procedures include Maintenance of alcohol intake, and Operant self-administration of alcohol.

Maintenance of Alcohol Intake

In this procedure sP rats were exposed to a 2-bottle free choice regimen between alcohol (10% v/v) and water. Under this condition, the animals can choose between a bottle containing the alcohol solution and a bottle containing water, and voluntarily consume about 6 g/kg/day of alcohol, with a preference for alcohol of about 90%. This procedure constitutes a valuable experimental model of the active drinking phase of human alcoholism; the alcohol intake of sP rats exposed to this model has been found to be reduced by drugs, such as GHB, naltrexone, and baclofen, that reduce craving for and consumption of alcohol in human alcoholics, demonstrating the predictive validity of this model.

Overall, experimental results demonstrated that the acute oral administration of ACGET61 at doses ranging from 25 to 100 mg/kg exerted a long-lasting reduction in alcohol consume without affecting water and food intake. Notably, ACGET61-induced reduction persisted even for 24 hours, as repeatedly observed in at least three independent experiments. The results of one of these experiments, expressed as cumulative consume of alcohol, water, and food, are reported in the FIG. 1.

In conclusion, the main improvement in the anti-alcohol activity of ACGET61 respect to its positional isomer GET 73, consisted in the duration of activity: GET 73 showed almost the same potency in reducing alcohol consume (10, 25, 50 mg/kg), but its effect lasted for only three hours (see Table 1 for the comparison; Loche et al., 2012).

Operant Self-Administration of Alcohol

In these procedures sP rats were trained to self-administer alcohol or sucrose by pressing a lever, and the amount of work (lever pressing) requested to obtain alcohol, varied according with the aim of the single schedule of reinforcement, Fixed ratio (FR) or Progressive ratio (PR).

Sucrose solution (3% w/v) was systematically employed in these experiments as alternative reinforcer, in order to assess if test compounds exert a selective effect on the alcohol solution (15% v/v) self-administration.

In the FR the rat obtain alcohol or sucrose in response to four consecutive lever pressing (FR4), while in the PR the number of lever pressing necessary to obtain alcohol or sucrose increased progressively till the rat stop pressing the lever (Break point; BP). Each FR4 or PR/BP session lasted 30 minutes.

Under these experimental conditions sP rats display a robust lever pressing behavior, demonstrating that alcohol possesses in this rat line strong reinforcing and motivational properties (Colombo et al., 2006).

FR4

Figure 2:
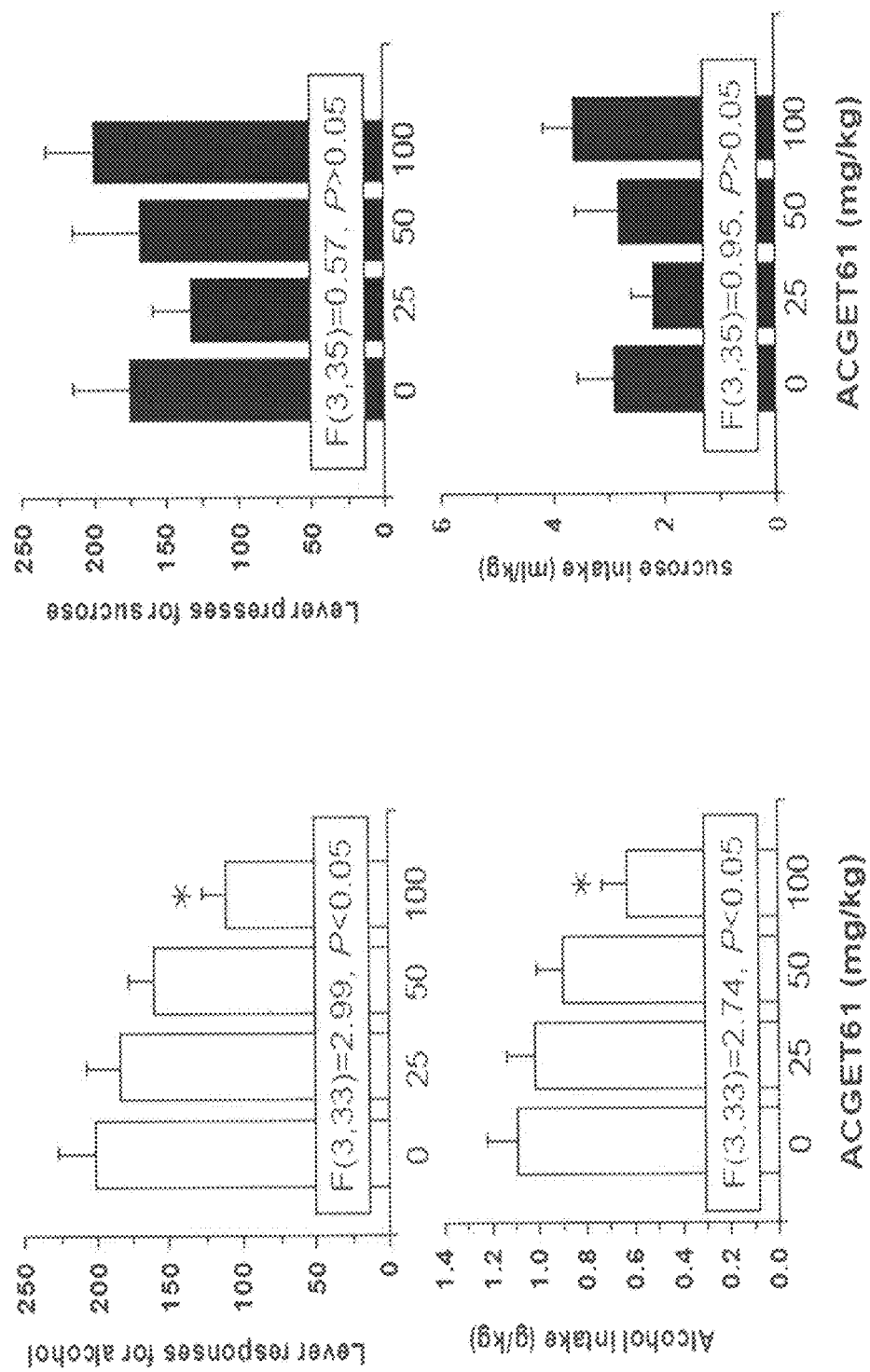
FIG. 2 shows bar graphs illustrating the effects of ACGET61 on FR4 operant self-administration of alcohol in sP rats.

ACGET61 100 mg/kg exerted a selective reducing effect on the reinforcing properties of alcohol in sP rats exposed to FR4 schedule of reinforcement, as shown in the FIG. 2, where the total number of lever responses and the amount of alcohol intake (g/kg) and of sucrose intake (ml/kg) in the 30 min session are reported. Specifically, FIG. 2 shows the effects of ACGET61 on FR4 operant self-administration of alcohol in sP rats. The number of lever pressing and the amount of alcohol or sucrose intake were reported. * $p<0.05$ vs vehicle-treated group.

PR/BP

Figure 3:
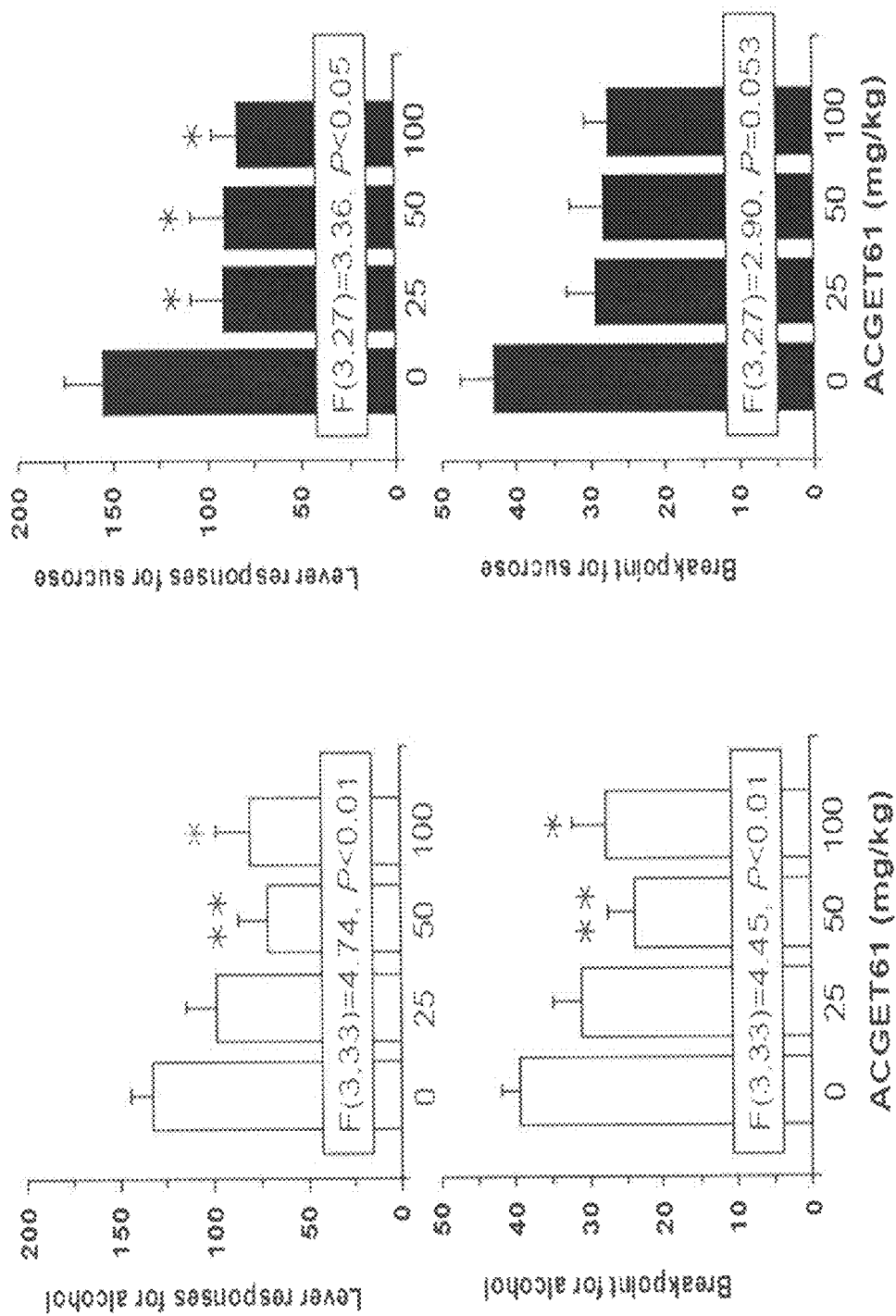
FIG. 3 shows bar graphs illustrating the effects of ACGET61 on PR operant self-administration of alcohol in sP rats.

ACGET61 50 and 100 mg/kg reduced both the number of lever pressing, and the break point for alcohol, in sP rats exposed to PR, even if the effect was not specific for alcohol, being the compound able to reduce also the response for sucrose, as evidenced in FIG. 3. Specifically, FIG. 3 shows the effects of ACGET61 on PR operant self-administration of alcohol in sP rats. The number of lever pressing and the break point for alcohol or sucrose were reported. * $p<0.05$ and ** $p<0.01$ vs vehicle-treated group.

Notably, GET73 did not demonstrate any effects in the same models, except for a significant reduction of sucrose intake in sP rats exposed to PR and administered with 50 mg/kg (see Table 1 hereinbelow for the comparison).

TABLE 1

Anti-alcohol profile of GET 73 and ACGET61 in sP rats.

| | GET 73 | | ACGET61 | |
|---|---|---|---|---|
| EXP. MODEL | Effective Doses mg/kg | Duration of effect | Effective Doses mg/kg | Duration of effect |
| Maintenance | 10-25-50 | 3 h | 25-50-100 | 24 h |
| FR4 | No effect (up to 50) | nd | 100 | nd |
| PR/BP | 50 # | nd | 50-100 * | nd | nd: not determined;
limited to sucrose;
* for alcohol and sucrose.

In Vitro Neurochemical Profile of ACGET61

Based on previous results obtained for GET 73, which influences the aminoacidergic neurotransmission in the rat hippocampus, probably through a complex modulation of the metabotropic glutamate receptors subtype 5 (mGluR5) (Beggiato et al., 2013; Ferraro et al., 2011, 2013) the positional isomer ACGET61 was evaluated in vitro in hippocampal slices, by measuring GABA and glutamate levels in different experimental conditions.

Effects of ACGET61 on Basal GABA and Glutamate Outflow

No effects was exerted by ACGET61 (10 and 100 μM) on the basal release of GABA and glutamate.

Effects of ACGET61 on $K^+$-Evoked GABA and Glutamate Outflow

Additional studies aimed at exploring the effect of ACGET61 (10 pM-10 μM) in KCl stimulated hippocampal slices were carried out.

Figure 4:
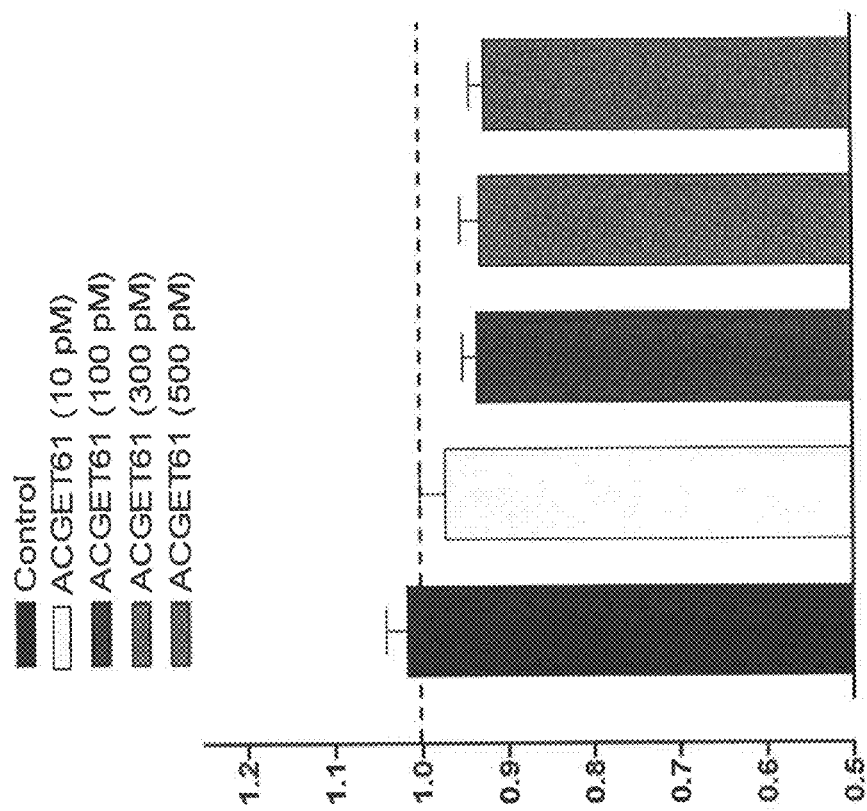
FIGS. 4 and 5 show bar graphs illustrating the K+ evoked glutamate outflow in Hippocampal slices.

ACGET61 at concentrations between 10 nM and 10 μM did not exert overt effects, except for the significant decrease in GABA induced by the highest concentration (data not shown). Concentration of ACGET61 lower than 10 nM, specifically 100, 300, and 500 pM induced a modest non significant reduction in the $K^+$-evoked glutamate outflow illustrated in the FIG. 4. Specifically, FIG. 4 shows effect of ACGET61 at pM concentrations on $K^+$ evoked glutamate outflow in the KCl stimulated Hippocampal slices.

Figure 5:
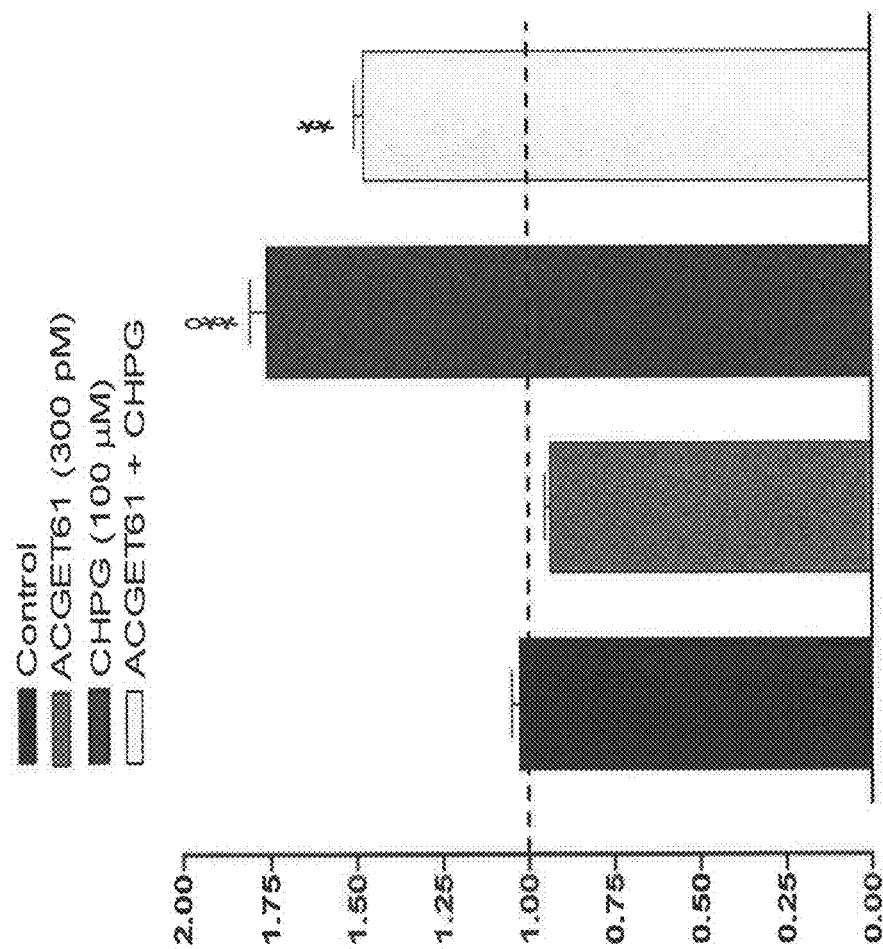

Effects of ACGET61 on the Increase in $K^+$-Evoked Glutamate Outflow Induced by the mGluR5 Receptor Agonist CHPG The interaction of ACGET61 with the mGluR5 agonist CHPG was explored in KCl stimulated hippocampal slices. The addition to the perfusion medium of ACGET61 300 pM (a concentration by itself ineffective) was able to counteract, at least in part, the increase in the $K^+$-evoked glutamate outflow exerted by CHPG, as shown in the FIG. 5. Specifically, FIG. 5—KCl stimulated Hippocampal slices—$K^+$ evoked glutamate outflow. The effect of ACGET61 300 pM on the increase in glutamate outflow induced by CHPG 100 μM. ** $p<0.01$ vs Control; ° $p<0.05$ vs ACGET61+CHPG.

This preliminary result indicated that ACGET61 possesses a neurochemical profile suggestive for a negative modulation at mGluR5. Notably, although additional studies aimed at exploring different pM concentrations should be performed, the potency of ACGET61 seemed greater in comparison with that exerted by GET 73 at 500 nM in the same model.

In Vitro Neuroprotective Profile of ACGET61

The neurotoxic effects of alcohol have been well documented, both in animals and humans, and the hippocampus represents a brain area particular sensitive to the detrimental effects of alcohol. Different preclinical models have been employed for studying the neurotoxic effects of alcohol. One of these models consists in exposing organotypic hippocampal cultures to alcohol, which exerts various effects, including a reduction in cell viability, and an increase in reactive oxygen species (ROS).

Based on previous results obtained for GET 73, which demonstrated an interesting neuroprotective profile in hippocampal cultures exposed to alcohol, ACGET61 was evaluated in the same model.

Briefly, primary cultures of rat hippocampal neurons were chronically exposed to ethanol (75 mM; 4 days) and the neuroprotective effects of ACGET61 were assessed by evaluating cell viability (MTT assay), and reactive oxygen species production (rhodamine 123 fluorescence).

ACGET61 was evaluated at different concentrations ranging between 0.01 and 10 μM and exerted positive effects on both the experimental parameters, increasing the cell viability, and decreasing ROS production in ethanol exposed hippocampal cultures.

MTT Assay

Figure 6:
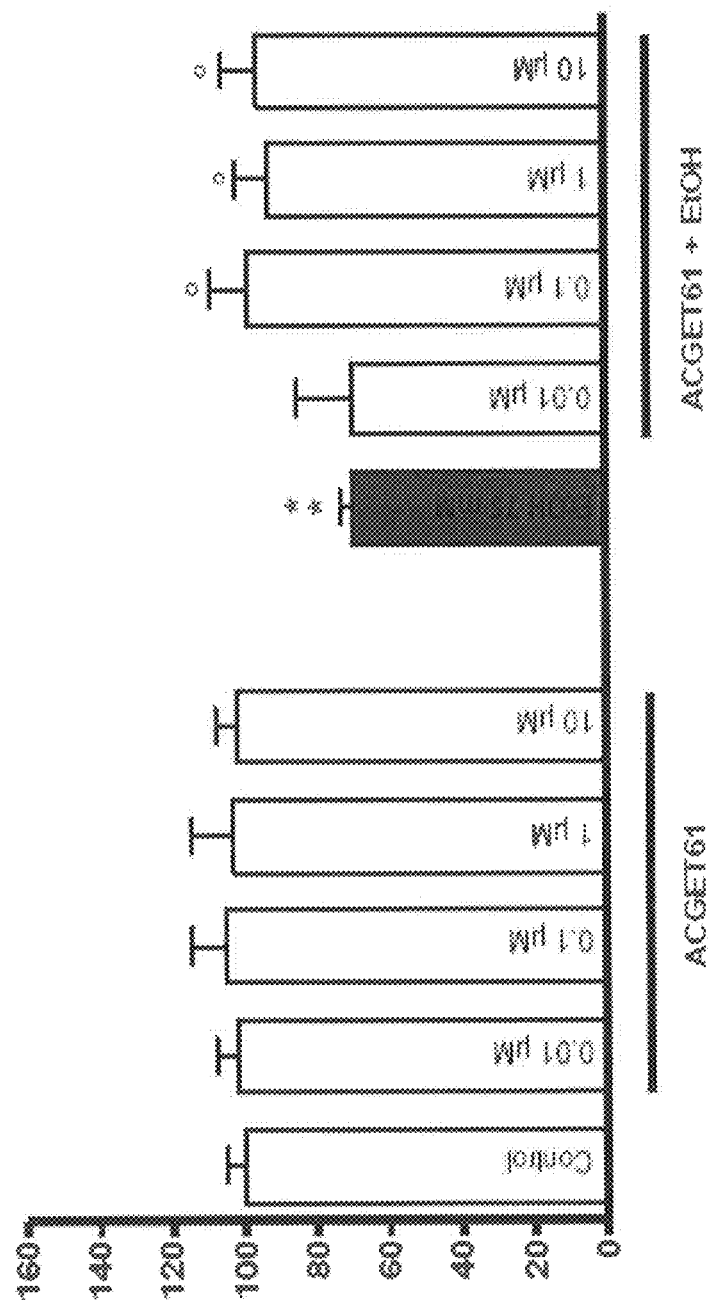
FIG. 6 shows the effects of ACGET61 on cell viability in hippocampal cell cultures exposed to ethanol (EtOH; 75 mM, 4 days)

The exposure to ethanol induced a decrease in cell viability as indicated by the significant decrease ($p<0.01$) of absorbance values respect to the control cell culture values. ACGET61 0.1, 1, and 10 μM added 1 hour before and during chronic ethanol exposure prevented the ethanol-induced damage, being the cell viability not significantly different respect to the control group, but significantly different respect to ethanol group ($p<0.05$). ACGET61 (0.01-10 μM) by itself did not affect cellular viability in hippocampal cell cultures not exposed to ethanol. The results, expressed as the percentage of neuronal viability measured in control cultures, are shown in the FIG. 6. Specifically, FIG. 6 shows the effects of ACGET61 on cell viability in hippocampal cell cultures exposed to ethanol (EtOH; 75 mM, 4 days) ** $p<0.01$ respect to control; °$p<0.05$ respect to EtOH 75 mM.

ROS Production

Ethanol exposure induced a significant increase in the ROS production ($p<0.001$), measured by the fluorescence emission of rhodamine 123.

The addition of ACGET61 0.1, 1, and 10 μM 1 h before and during chronic ethanol exposure prevented the ethanol-induced increase of ROS production, being the ROS production not significantly different respect to the control group, but significantly different respect to ethanol group ($p<0.01$; $p<0.001$).

Figure 7:
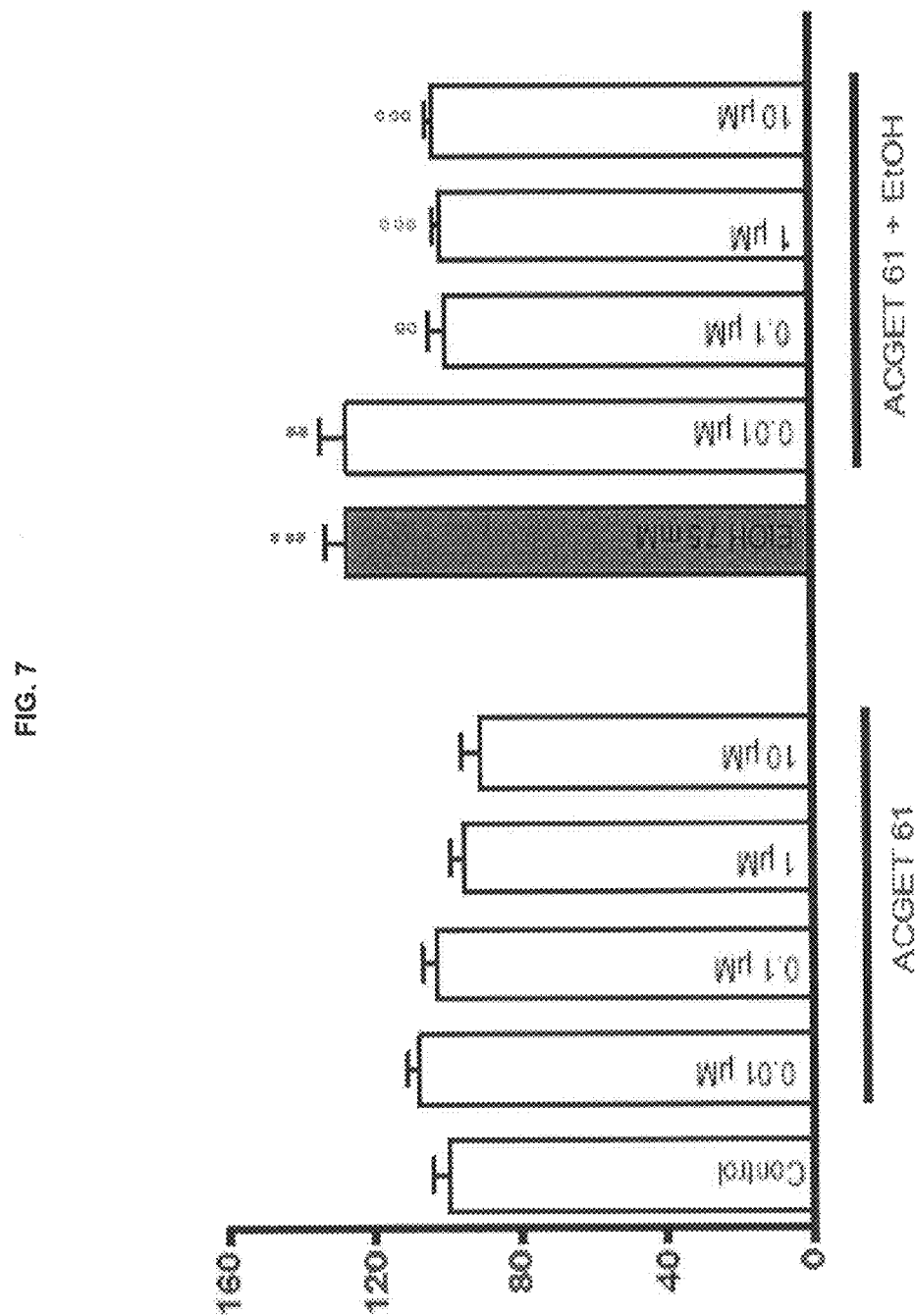
FIG. 7 shows the effects of ACGET61 on ROS production in hippocampal cell cultures exposed to ethanol (EtOH; 75 mM, 4 days)

ACGET61 (0.01-10 μM) by itself did not affect ROS production in hippocampal cell cultures not exposed to ethanol. The results, expressed as the percentage of ROS production measured in control cultures, are shown in the FIG. 7. Specifically, FIG. 7 shows the effects of ACGET61 on ROS production in hippocampal cell cultures exposed to ethanol (EtOH; 75 mM, 4 days). $p<0.01$, *$p<0.001$ respect to control; °°$p<0.01$, °°°$p<0.001$ respect to EtOH 75 mM.

Notably, these neuroprotective effects were exerted by ACGET61 at 0.1, 1, and 10 μM, suggesting greater potency respect to its positional isomer GET 73: in fact the minimum effective concentration for ACGET61 was 0.1 μM vs 1 μM for GET 73.

Example 3

Pharmaceutical Composition

| | |
|---|---:|
| N-[(2-trifluoromethyl)benzyl]-4-methoxybutyramide (ACGET61) | 50 mg |
| Cellulose mycrocrystalline (as appropriate disintegrant) | 60 mg |
| Talc (as lubricant) | 10 mg |
| Sodium laurylsulfate (as surfactant) | 5 mg |
| Calcium phosphate (as aggregant-diluent) | 200 mg |
| Magnesium carbonate (as diluent-binder) | 100 mg |

Example 4

Pharmaceutical Composition

| | |
|---|---:|
| N-[(2-trifluoromethyl)benzyl]-4-methoxybutyramide (ACGET61) | 150 mg |
| Maize starch (as appropriate disintegrant) | 100 mg |
| Glyceryl behenate (as lubricant) | 10 mg |
| Polysorbate (as surfactant) | 10 mg |
| Magnesium carbonate (as diluent-binder) | 150 mg |
| Lactose (as diluent) | 150 mg |

Example 5

Pharmaceutical Composition with Film-Coating/Modified Release

| | |
|---|---|
| N-[(2-trifluoromethyl)benzyl]-4-methoxybutyramide (ACGET61) | 500 mg |
| Cellulose mycrocrystalline (as appropriate disintegrant) | 200 mg |
| Crospovidone (as anti-aggregant agent) | 50 mg |
| Starch (as diluent-disintegrant) | 50 mg |
| Colloidal silica (as drying agent) | 10 mg |
| Magnesium stearate (as lubricant) | 10 mg |
| Hypromellose (as coating agent) | 50 mg |
| Macrogol (as plasticiser agent) | 10 mg |
| Titanium dioxide (as dye) | 10 mg |

The invention claimed is:

1. A compound of Formula (I):

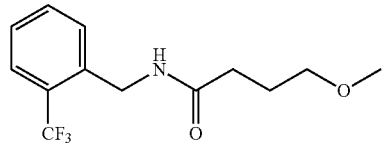

Formula (I)

or a pharmaceutically acceptable salt thereof.

2. A pharmaceutical composition comprising a compound according to claim 1 and a pharmaceutically acceptable carrier.

3. A pharmaceutical composition according to claim 2 wherein the compound of formula (I) is present in an amount of 50 to 500 mg.

* * * * *